(12) United States Patent
Agarwal et al.

(10) Patent No.: US 9,645,994 B2
(45) Date of Patent: May 9, 2017

(54) METHODS AND SYSTEMS FOR AUTOMATIC ANALYSIS OF CONVERSATIONS BETWEEN CUSTOMER CARE AGENTS AND CUSTOMERS

(71) Applicant: XEROX CORPORATION, Norwalk, CT (US)

(72) Inventors: Arvind Agarwal, Rochester, NY (US); Saurabh Kataria, Rochester, NY (US); Tong Sun, Penfield, NY (US); Sumit Bhatia, Webster, NY (US)

(73) Assignee: Conduent Business Services, LLC, Dallas, TX (US)

( * ) Notice: Subject to any disclaimer, the term of this patent is extended or adjusted under 35 U.S.C. 154(b) by 163 days.

(21) Appl. No.: 14/564,170

(22) Filed: Dec. 9, 2014

(65) Prior Publication Data
US 2016/0162474 A1 Jun. 9, 2016

(51) Int. Cl.
*G06F 17/27* (2006.01)
*G06Q 30/00* (2012.01)
(Continued)

(52) U.S. Cl.
CPC .......... *G06F 17/274* (2013.01); *G06F 17/279* (2013.01); *G06F 17/2765* (2013.01);
(Continued)

(58) Field of Classification Search
CPC .... G06F 19/24; G06N 99/005; G06N 3/0472; G10L 15/06; G10L 15/063;
(Continued)

(56) References Cited

U.S. PATENT DOCUMENTS 7,457,745 B2 * 11/2008 Kadambe ................ G10L 15/07
704/216
8,086,549 B2 * 12/2011 Qi ......................... G06N 99/005
706/14
(Continued)

OTHER PUBLICATIONS

Agarwal, A., III Daume, H., and Gerber, S. Learning multiple tasks using manifold regularization. In Advances in neural information processing systems (2010), pp. 46-54.
(Continued)

*Primary Examiner* — Richard Zhu
(74) *Attorney, Agent, or Firm* — Jones Robb PLLC

(57) ABSTRACT

The technical solution under the present disclosure automatically analyzes conversations between users by receiving a training dataset having a text sequence including sentences of a conversation between the users; extracting feature(s) from the training dataset based on features; providing equation(s) for a plurality of tasks, the equation(s) being a mathematical function for calculating value of a parameter for each of the tasks based on the extracted feature; determining value of the parameter for tasks by processing the equation(s); assigning label(s) to each of the sentences based on the determined value of the parameter, a first label being selected from a plurality of first labels, and a second label being selected from a number of second labels; and storing and maintaining with the database a pre-defined value of the parameter, first labels, conversations, second labels, a test dataset, equation(s), and pre-defined features.

27 Claims, 8 Drawing Sheets

(51) Int. Cl.
  G06Q 50/00    (2012.01)
  G10L 15/06    (2013.01)
  G06F 19/24    (2011.01)
  G06N 99/00    (2010.01)

(52) U.S. Cl.
  CPC ......... *G06F 17/2775* (2013.01); *G06Q 30/00* (2013.01); *G06Q 50/01* (2013.01); *G06F 19/24* (2013.01); *G06N 99/005* (2013.01); *G10L 15/06* (2013.01)

(58) Field of Classification Search
  CPC ..... G10L 2015/0631; G10L 2015/0633; G10L 2015/0635; G10L 2015/0636; G10L 2015/0638
  See application file for complete search history.

(56) References Cited

U.S. PATENT DOCUMENTS

| | | | | |
|---|---|---|---|---|
| 8,504,361 | B2* | 8/2013 | Collobert | G06F 17/277 704/232 |
| 8,554,555 | B2* | 10/2013 | Gruhn | G10L 15/063 704/232 |
| 8,843,368 | B2* | 9/2014 | Kim | G10L 15/265 704/231 |
| 8,990,126 | B1* | 3/2015 | Bangalore | G06F 17/211 706/12 |
| 2008/0249764 | A1* | 10/2008 | Huang | G06F 17/2785 704/9 |
| 2010/0114575 | A1* | 5/2010 | Itoh | G10L 15/26 704/251 |
| 2010/0145678 | A1* | 6/2010 | Csomai | G06F 17/2755 704/9 |
| 2012/0130771 | A1* | 5/2012 | Kannan | G06Q 10/06398 705/7.32 |
| 2012/0150531 | A1* | 6/2012 | Bangalore | G06F 17/28 704/9 |
| 2013/0132331 | A1* | 5/2013 | Kowalczyk | G06N 99/005 706/52 |
| 2015/0066479 | A1* | 3/2015 | Pasupalak | G06F 17/27 704/9 |
| 2015/0287402 | A1* | 10/2015 | Okabe | H04M 3/4936 704/249 |

OTHER PUBLICATIONS

Argyriou, A., Micchelli, C. A., Pontil, M., and Ying, Y. A spectral regularization framework for multi-task structure learning. In NIPS '08. 2008.
Belkin, M., Niyogi, P., and Sindhwani, V. Manifold regularization: A geometric framework for learning from labeled and unlabeled examples. J. Mach. Learn. Res. 7 (2006), 2399-2434.
Caruana, R. Multitask learning. In Machine Learning (1997), pp. 41-75.
Daume III, H. Bayesian multitask learning with latent hierarchies. In Conference on Uncertainty in Artificial Intelligence '09 (Montreal, Canada, 2009).
Evgeniou, T., Micchelli, C. A., and Pontil, M. Learning multiple tasks with kernel methods. JMLR 6 (2005), 615-637.
Jacob, L., Bach, F., and Vert, J.-P. Clustered multi-task learning: A Convex formulation. In NIPS '08 (2008).
Liu, Q., Liao, X., Carin, H. L., Stack, J. R., and Carin, L. Semisupervised multitask learning. IEEE 2009 (2009).
Evgeniou and Pontil, M. Regularized multi-task learning. In KDD 2004 (2004), pp. 109-117.
Schwaighofer, A., Tresp, V., and Yu, K. Learning gaussian process kernels via hierarchical Bayes. In Advances in Neural Information Processing Systems (2004), pp. 1209-1216.
Sutton, C., McCallum, A., and Rohanimanesh, K. Dynamic conditional random fields: Factorized probabilistic models for labeling and segmenting sequence data. The Journal of Machine Learning Research 8 (2007), 693-723.
Tjong Kim Sang, E. F., and Buchholz, S. Introduction to the conll-2000 shared task: Chunking. In Proceedings of the 2nd workshop on Learning language in logic and the 4th conference on Computational natural language learning—vol. 7 (2000), Association for Computational Linguistics, pp. 127-132.
Xue, Y., Liao, X., Carin, L., and Krishnapuram, B. Multi-task learning for classification with dirichlet process priors. J. Mach. Learn. Res. 8 (2007), 35-63.
Yu, K., Tresp, V., and Schwaighofer, A. Learning gaussian processes from multiple tasks. In ICML '05 (2005).

* cited by examiner

METHODS AND SYSTEMS FOR AUTOMATIC ANALYSIS OF CONVERSATIONS BETWEEN CUSTOMER CARE AGENTS AND CUSTOMERS

TECHNICAL FIELD

The presently disclosed embodiments relate to customer relationship management (CRM) systems, and more particularly to methods and systems for automatically analyzing conversations between social CRM agents and customers.

BACKGROUND

Customer Relationship Management (CRM) relates to various models and technologies for managing a company's relationships with its existing, past, and future customers. Some related art CRM systems automate, organize, and synchronize marketing, sales, customer service, and technical support. Customer engagement can be a critical component of social CRM solutions, wherein customer care agents contact customers via social media, and resolve their issues by engaging in asynchronous conversations with the customers. Some CRM systems integrate social media sites like Twitter, LinkedIn, and Facebook to track and communicate with customers to share their opinions and experiences with a company, products and services. The social media is a platform that connects millions of users together, and allows them to exchange and share common interests, topics or events. These platforms had been developed for private usage among users, and later emerged as a new communication and marketing vector for the companies. Social media has grown at a consistent rate, and has become very relevant in the context of brand information.

Related art CRM solutions/systems provide a mechanism for the customer care agents to engage in conversations with customers to address their issues via telephone calls. Two new communication channels that were later used by CRM teams include synchronous online chat and emails provided by social media. CRM solutions need to constantly monitor the conversations, mainly for two components of the conversation, in order to provide an effective engagement. First, the status of the issue (issue status tracking) that is relevant to the conversation relates to customer satisfaction. Second, the nature of the dialogues (dialogue act tracking) engaged in by the agents relate to the effectiveness of the customer care agents and the conversation.

SUMMARY

The issue status tracking is significant because interaction between a customer and a customer care agent takes place over a long period of time, during which the agent needs to return to the issues multiple times and address the customer's concern. Since one agent is usually involved with thousands of users at the same time, the agent needs to return to only the open issues. The agent should not spend time checking the resolved issues. Given the large number of customers and their data, it is important that the process of figuring out which issues are open and which are closed is automated. The dialogue act problem is important because it determines the nature of the dialogue that agents engage in with the customer. For example, the dialogue can be a simple greeting message, an acknowledgement, or a more involved statement that addresses the issue in a technical way. This dialogue act component helps CRM solutions to determine the effectiveness of the customer care agents and of conversations.

Typically, machine learning methods, such as supervised classification techniques, are employed to analyze these conversations that can track and measure effectiveness of these conversations in terms of issue resolution (issue status) and the nature of the dialogues that customer care agents engage in (i.e., dialogue act). However, due to the very sparse and informal nature of these social media conversations, existing machine learning techniques are not very accurate in terms of detecting issues status and dialogue act.

Usually, to determine the status of an issue, a supervised machine learning based technique is employed to learn a model from the issues whose statuses are already identified, and the statuses of the incoming issues are identified based using the learnt model. Similarly, a model (separate from the issues tracking model) is learned to address the dialogue act problem. However, intuitively, these two tasks are closely related, and they share similarities in feature space, i.e., most of the issues that are resolved end with customer thanking for agent's help. Therefore, it makes more sense to learn these two tasks simultaneously. That is, labels assigned to issue resolution task (or status issue task) can help to learn a better model for dialogue act task (or nature of the conversation task), and vice versa. In this disclosure, a multi-task learning method is disclosed, which learns from such two tasks that share features, simultaneously, and show that the learning of two tasks simultaneously can improve the accuracy for both tasks.

An embodiment of the present disclosure provides a method for automatically analyzing conversations between multiple users. The method includes receiving, by a data collecting module, a training dataset having a natural language text sequence including a number of sentences of a conversation between the users. Each of the sentences includes a number of words. The method further includes extracting, by a feature extracting module, at least one feature from the training dataset based on a number of pre-defined features stored in a database. The method furthermore includes providing, by a parameter determining module, at least one equation for each of a plurality of tasks. The at least one equation being a mathematical function capable of calculating value of at least one parameter for each of the tasks based on the extracted at least one feature for the tasks. The method also includes determining, by the parameter determining module, a value of the at least one parameter for each of the tasks by processing the at least one equation of the tasks. The method further includes assigning, by a labeling module, one or more labels to each of the sentences based on the determined value of the at least one parameter. A first label of the one or more labels being selected from a plurality of first labels, and a second label of the one or more labels being selected from a plurality of second labels. The method also includes storing and maintaining, in a database, with the database a pre-defined value of the at least one parameter, the first labels, a number of conversation, the second labels, a test dataset, the at least one equation, and the pre-defined features. The test dataset includes a pre-defined set of sentences including at least one word.

Another embodiment of the present disclosure provides a conversation analysis system for automatically analyzing conversations between a number of users. The conversation analysis system includes a data collecting module configured to receive a training dataset. The training dataset includes a natural language text sequence including a number of sentences of a conversation between the users. Each of the sentences includes a number of words. The conversation analysis system also includes a database configured to store pre-defined value of at least one parameter, a number of pre-defined features, a number of conversations, a number of first labels, a number of second labels, and a test dataset. The test dataset includes a pre-defined set of sentences including at least one word. The conversation analysis system further includes a feature extracting module configured to extract at least one feature from each of the plurality of sentences based on the pre-defined features stored in the database. The conversation analysis system further includes a parameter determining module configured to provide at least one equation for each of a number of tasks. The at least one equation being a mathematical function capable of calculating value of at least one parameter for each of the tasks based on the extracted at least one feature for the tasks. The parameter determining module is further configured to determine value of each of the at least one parameter for each of the tasks by processing the at least one equation for each of the tasks. The conversation analysis system also includes a labeling module configured to assign one or more labels to each of the plurality of sentences based on the determined value of the at least one parameter. A first label of the one or more labels being selected from the first labels, and a second label of the one or more labels being selected from the second labels stored in the database.

A yet another embodiment of the present disclosure provides a method for automatically analyzing conversations between a customer care agent and a plurality of customers. The method includes receiving, by a data collecting module, a training dataset having a natural language text sequence including a number of sentences of a conversation between the customer agent and the customers. Each of the sentences includes a number of words. The method also includes extracting, by a feature extracting module, at least one feature from the training dataset based on a number of pre-defined features stored in a database. The method further includes providing, by a parameter determining module, at least one equation for each of a number of tasks. The at least one equation being a mathematical function capable of calculating value of at least one parameter for each of the tasks based on the extracted at least one feature for the tasks. The at least one equation includes a common parameter for each of the tasks. The method also includes determining, by the parameter determining module, a value for the at least one parameter for each of the tasks by processing the at least one equation of the tasks. The method further includes assigning, by a labeling module, one or more labels to each of the plurality of sentences based on the determined value of the at least one parameter. A first label of the one or more labels is selected from a plurality of first labels, and a second label of the one or more labels is selected from a plurality of second labels. The method also includes evaluating, by an evaluating module, the determined value of the at least one parameter by comparing the determined value of the at least one parameter with a pre-defined value of the at least one parameter stored in the database. The pre-defined value of the at least one parameter is obtained based on a test dataset. The method further includes storing and maintaining, in a database, with the database the pre-defined value of the at least one parameter, the plurality of first labels, a plurality of conversation, the plurality of second labels, the at least one equation, and a test dataset, wherein the test dataset includes a pre-defined set of sentences including at least one word.

A further embodiment of the present disclosure provides a conversation analysis system. The conversation analysis system includes a database configured to store and maintain a plurality of conversations, a pre-defined value of the at least one parameter, a plurality of pre-defined features, a plurality of first labels, a plurality of second labels, at least one equation, and a test dataset, the test dataset including a pre-defined set of sentences including at least one word. The system also includes a data collecting module configured to receive a training dataset having a natural language text sequence including a plurality of sentences of a conversation between a plurality of users, each of the plurality of sentences includes a number of words. The system further includes a feature extracting module configured to extract at least one feature from the training dataset based on the plurality of pre-defined features stored in the database. The system also includes a parameter determining module configured to provide at least one equation for each of at least two tasks, the at least one equation being a mathematical function capable of calculating value of at least one parameter for each of the at least two tasks based on the extracted at least one feature for the at least two tasks, the at least one equation including a common parameter for each of the at least two tasks. The parameter determining module is also configured to determine value of the at least one parameter for each of the at least two tasks by processing the at least one equation for each of the at least two tasks. The system also includes a labeling module configured to assign one or more labels to each of the plurality of sentences based on the determined value of the at least one parameter. A first label of the one or more labels being selected from the plurality of first labels, and a second label of the one or more labels being selected from the plurality of second labels. Further, the system includes an evaluating module configured to evaluate determined value of the at least one parameter by comparing the determined value of the at least one parameter with the pre-defined value of the at least one parameter stored in the database. The pre-defined value of the at least one parameter is obtained based on a test dataset. The test dataset includes a pre-defined set of sentences including at least one word.

A yet another embodiment of the present disclosure provides a computer readable medium and computer program instructions, recorded on the computer readable medium executable by a processor, for performing the steps of: receiving a training dataset having a natural language text sequence including multiple sentences of a conversation between the users, each of the sentences includes a number of words; extracting at least one feature from the training dataset based on a number of pre-defined features stored in a database; providing at least one equation for each of a number of tasks, the at least one equation being a mathematical function capable of calculating value of at least one parameter for each of the tasks based on the extracted at least one feature for the tasks; determining value of the at least one parameter for each of the tasks by processing the at least one equation of the tasks; assigning one or more labels to each of the plurality of sentences based on the determined value of the at least one parameter, wherein a first label of the one or more labels is selected from a plurality of first labels and a second label of the one or more labels is selected from a plurality of second labels; and storing and maintaining in the database a pre-defined value of the at least one parameter, the plurality of first labels, a plurality of conversation, the plurality of second labels, a test dataset, the at least one equation, and the plurality of pre-defined features, wherein the test dataset includes a pre-defined set of sentences including at least one word.

DETAILED DESCRIPTION

Figure 1A:
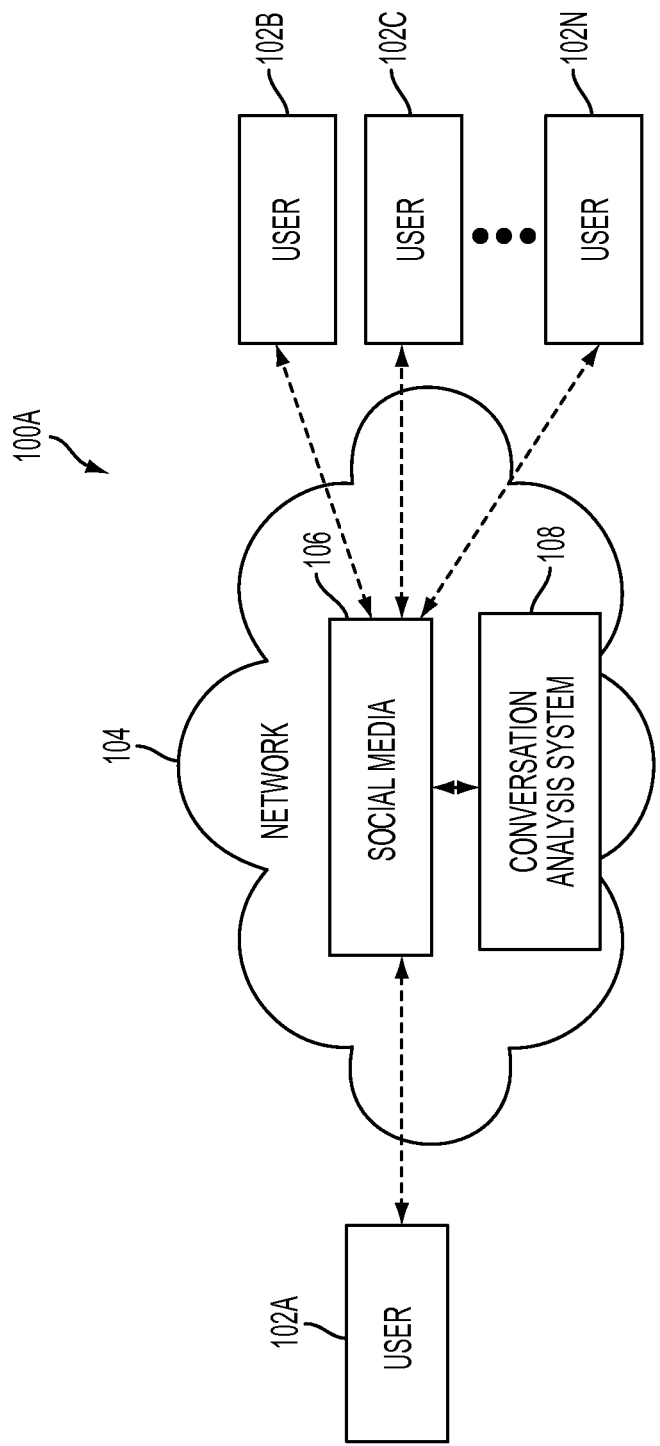
FIG. 1A is a schematic illustrating an exemplary system in accordance with an embodiment of the present disclosure.

The following detailed description is made with reference to the figures. Preferred embodiments are described to illustrate the disclosure, not to limit its scope, which is defined by the claims. Those of ordinary skill in the art will recognize a number of equivalent variations in the description that follows.

Definitions:

In this disclosure, the term 'Customer Relationship Management (CRM)' refers to use of various models and technologies for managing a company's relations with their existing, past, and future customers. The term 'CRM system' refers to a system for automating, organizing, and synchronizing marketing, sales, customer service and technical support in a company. The CRM system may be include software, hardware, or combination of hardware and software. As used herein, a social CRM system refers to a CRM system, which entails customer care agents to contact customers via social media, and resolve their issues by having asynchronous conversations with them over the social media. The term 'social media' may refer to a platform that connects millions of users together, and allows them to exchange and share common interests, topics or events. Some social CRM systems integrate social media sites like Twitter, LinkedIn, and Facebook to track and communicate with customers sharing their opinions and experiences with a company, products and services.

As used herein, a 'training dataset' includes a natural language text sequence including a number of sentences of a conversation that happen between a number of users such as, between a customer care agent and a number of customers. The term 'sentence' refers to a sequence of words in a particular language. The term 'feature' or 'feature vector' defines a property of an entity such as a sentence, a person or an object. Hereinafter, the term 'feature' and 'feature vector' are used interchangeably.

The term 'equation' refers to a mathematical function capable of calculating value of one or more variables. Further, the term 'task' refers to a problem, which needs to be solved. In the present disclosure, a task may refer to a problem to determine a status of an issue in a conversation and a problem to determine the nature of the conversation. As used herein, a 'test dataset' includes a number of sentences of a conversation that occurs between a customer care agent and a number of customers using a social media.

Further, a 'conversation analysis system' may be a combination or software, hardware, firmware, or combination of these, for analyzing the conversation between different users or between a customer care agent and a number of customers. The conversation analysis system is further intended to include or otherwise cover all software or computer programs capable of performing the various heretofore-disclosed determinations, calculations, etc., for the disclosed purposes. For example, exemplary embodiments are intended to cover all software or computer programs capable of enabling processors to implement the disclosed processes. Exemplary embodiments are also intended to cover any and all currently known, related art or later developed non-transitory recording or storage mediums (such as a CD-ROM, DVD-ROM, hard drive, RAM, ROM, floppy disc, magnetic tape cassette, etc.) that record or store such software or computer programs. Exemplary embodiments are further intended to cover such software, computer programs, systems and/or processes provided through any other currently known, related art, or later developed medium (such as transitory mediums, carrier waves, etc.), usable for implementing the exemplary operations disclosed below.

In accordance with the exemplary embodiments, the disclosed computer programs can be executed in many exemplary ways, such as an application that is resident in the memory of a device or as a hosted application that is being executed on a server and communicating with the device application or browser via a number of standard protocols, such as TCP/IP, HTTP, XML, SOAP, REST, JSON and other sufficient protocols. The disclosed computer programs can be written in exemplary programming languages that execute from memory on the device or from a hosted server, such as BASIC, COBOL, C, C++, Java, Pascal, or scripting languages such as JavaScript, Python, Ruby, PHP, Perl or other sufficient programming languages.

Some of the disclosed embodiments include or otherwise involve data transfer over a network, such as communicating various inputs over the network. The network may include, for example, one or more of the Internet, Wide Area Networks (WANs), Local Area Networks (LANs), a personal area network (PAN), a storage area network (SAN), a home area network (HAN), a campus area network (CAN), analog or digital wired and wireless telephone networks (e.g., a PSTN, Integrated Services Digital Network (ISDN), a metropolitan area network (MAN), a virtual private network (VPN), an enterprise private network (EPN), Internet, a global area network (GAN), a cellular network, and Digital Subscriber Line (xDSL)), radio, television, cable, satellite, and/or any other delivery or tunneling mechanism for carrying data. Network may include multiple networks or subnetworks, each of which may include, for example, a wired or wireless data pathway. The network may include a circuit-switched voice network, a packet-switched data network, or any other network able to carry electronic communications. For example, the network may include networks based on the Internet protocol (IP) or asynchronous transfer mode (ATM), and may support voice using, for example, VoIP, Voice-over-ATM, or other comparable protocols used for voice data communications. In one implementation, the network includes a cellular telephone network configured to enable exchange of text or SMS messages.

The client and server devices are intended to include or otherwise cover all software or computer programs capable of performing the various heretofore-disclosed determinations, calculations, etc., for the disclosed purposes. For example, exemplary embodiments are intended to cover all software or computer programs capable of enabling processors to implement the disclosed processes.

Overview:

Embodiments of the present disclosure relate to a method that allows automatic analysis of logs of conversations between a social CRM (Customer Relationship Management) agent and customers to identify the current state of issue resolution as well as overall engagement effectiveness of conversation in terms of customer satisfaction, etc. A conversation may include a natural language sequence of sentences that are exchanged between a plurality of users such as a customer care agent and customer(s).

Typically, for a task such as a task to determine the status of an issue, a supervised machine learning based technique is employed to learn a model from the issues whose statuses are already identified. In addition, the statuses of the incoming issues are identified based using the learned model. Similarly, a separate model is used for another task, such as a task, to determine labels for dialogue act problem (or statements analysis). However, intuitively, these two tasks are closely related. That is labels assigned to issue resolution task can help to learn a better model for dialogue act task and vice versa. In present disclosure, multi-task learning methods and systems are disclosed to learn from such two tasks that may share features simultaneously. Further, learning these two tasks simultaneously can improve the accuracy for both the tasks. The proposed method combines a linguistic framework and machine learning framework of labeling sequences to automatically label messages/sentences in the conversation.

The present disclosure provides a learning framework for sequence classification that can take multiple labeled sequences and learn from them simultaneously. Further, a framework for conversation classification is disclosed that can identify a customer's issue status as well as dialogue act (or nature of the conversation) of the interaction between a customer and a customer care agent.

The present disclosure further discloses a method that not only exploits the label dependency but also learns the multiple tasks simultaneously by explicitly sharing the parameters corresponding to the label dependency factor. In the disclosed method, a model for each task i.e. issue status determining task and nature of conversation determining task. Each model (or equation) includes a set of factors for its own task with one additional one factor for the label dependency part. The parameters corresponding to the label dependency factor may remain common among all the tasks. An unshared version is also disclosed herein.

Exemplary Embodiments

FIG. 1A is a schematic that illustrates an exemplary system 100A, in accordance with an embodiment of the present disclosure. To analyze the present disclosure, the system 100A can be visualized as having the following primary components, one or more users 102, a network 104, a social media 106, and a conversation analysis system 108. The users 102A-102N are capable of communicating with each other via the social media 106. The social media 106 may be a website, which facilitates various users 102A-102N to make and manage a social network including other users over the network 104 such as the Internet. The social media 106 provides a platform that connects million of the users 102A-102N together, and allows them to exchange and share common interests, topics or events. In some embodiments, the conversation analysis systems integrate social media 106 like Twitter, LinkedIn, and Facebook to track and communicate with customers sharing their opinions and experiences with a company, products and services. The social media 106 may be a social networking website, a blogging website, an e-commerce website. Examples of the social networking sites may include, but are not limited to, Twitter, Facebook. LinkedIn, MySpace, Faceparty, Exploroo, Friendster, Kiwibox, and so forth. The users 102A-102N may access the social media 106 via the network 104. Examples of the network 104 may include, but are not limited to, the Internet, local area network (LAN), wide area network (WAN), and so forth.

The conversation analysis system 108 may be part of a customer relationship management (CRM) system. The conversation analysis system 108 is configured to collect/record and/or analyze the conversations that happen between the users 102A-102N using the social media 106.

Figure 1B:
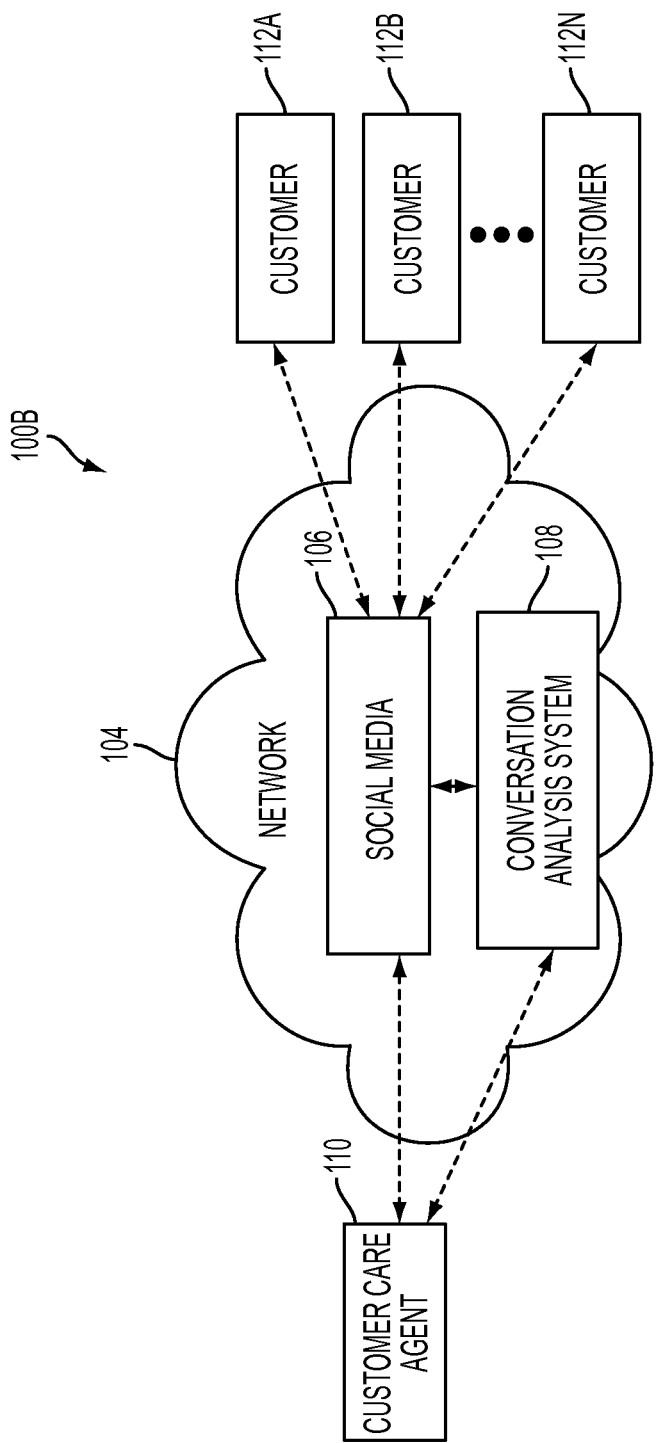
FIG. 1B is a schematic illustrating another exemplary system, in accordance with another embodiment of the present disclosure.

In an embodiment, the conversation analysis system 108 is configured to analyze the conversation that happen between a customer care agent 110 and a number of customers 112A-112N as shown in system 100B in FIG. 1B. Further, the conversation analysis system 108 is configured to analyze the conversation as a training dataset and at sentence level. In some embodiments, the training dataset includes a natural language text sequence including a number of sentences, phrases, clauses, clichés, and similar text sequences of a conversation that happen between the users 102A-102N (or between a customer care agent and a number of customers). The sentence, in turn may include multiple words of a particular language. Examples of the natural language may include, such as, but not limited to, English, Hindi, French, Spanish, and so forth. The conversation analysis system 108 defines at least one equations for analyzing the conversation. This is discussed further with reference to FIGS. 2A-2B.

Figure 2A:
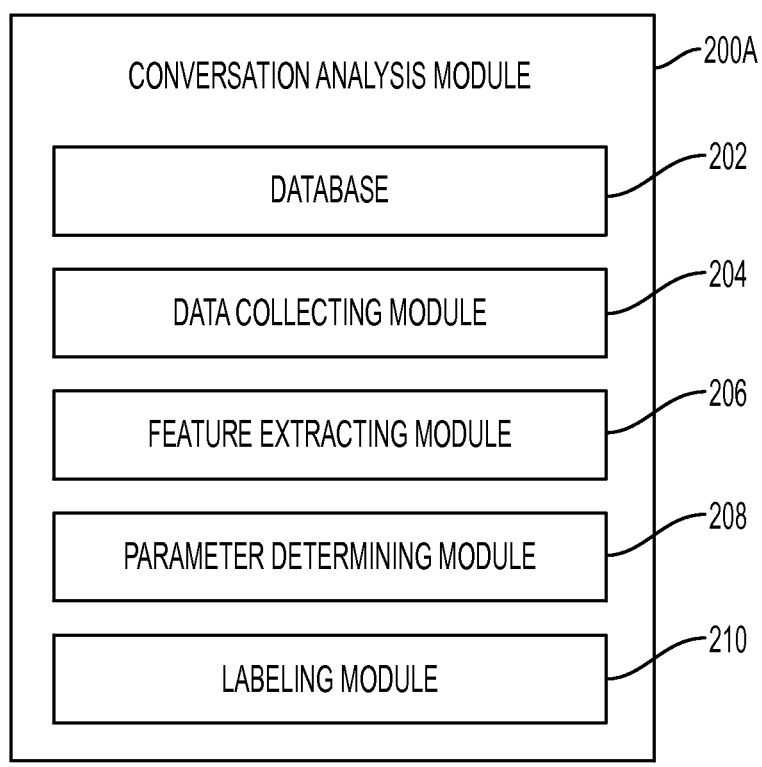
FIG. 2A is a schematic illustrating structural components of a conversation analysis system, in accordance with an embodiment of the present disclosure.

FIG. 2A is a schematic that illustrates structural components of a conversation analysis system 200A, in accordance with an embodiment of the present disclosure. As shown, the conversation analysis system 200A is similar to the conversation analysis system 108 shown in FIGS. 1A-1B. The conversation analysis system 200A includes a database 202, a data collecting module 204, a feature extracting module 206, a parameter determining module 208, and a labeling module 210. In an embodiment, the conversation analysis system 200A is configured to automatically analyze conversations that happen between a number of users such as, the users 102A-102N as shown in FIG. 1A. The users 102A-102N may be the customer care agent and the customers 112A-112N, as shown in FIG. 1B.

The database 202 is configured to store conversations, pre-defined value of at least one parameter, a number of pre-defined features, a number of first labels, a number of second labels, and a test dataset. The conversation includes a number of statements having multiple words, phrases, clauses, clichés, and similar text sequences. The feature may define a property associated with an entity such as a sentence. For example, number of words in a sentence is a feature of the sentence.

The data collecting module 204 is configured to collect or receive a training dataset. The training dataset may be received from the social media 106 such as Twitter. The training dataset may be a subset of the one or more conversations to be analyzed. Further, the training dataset may include a natural language text sequence including one or more sentences of a conversation that happen or happened between the users 102A-102N and/or between the customer care agent 110 and the customers 112A-112N. Further, each of the one or more sentences may include a number of words. Examples of the language may include, but not limited to, English, Hindi, French, and so forth.

Further, the feature extracting module 206 is configured to extract at least one feature from each of the one or more sentences of the conversation being analyzed. The features may be extracted based on the pre-defined features stored in the database 202. For each of the one or more sentences in a conversation, the feature extracting module 206 is configured to automatically associate a set of features to it. Further, the feature extracting module 206 may associate the set of features with the sentences based on the feature, feature type and feature description of the feature as mentioned in Table 1.

TABLE 1

| Feature | Feature Type | Feature Description |
| --- | --- | --- |
| Word 1-grams and 2-grams | 1 integer/n-gram | The count of n-grams of words that compose the tweet segment |
| Segment position in thread | Integer | Position of the tweet in the thread |
| Segment position in tweet | Integer | Position of the segment in the tweet |
| Sender | Boolean | CRM agent or customer |
| Contains email | Boolean | Presence of an email in the tweet segment |
| # upper case | Integer | % of letters in upper case in the tweet segment |
| # punctuation | Integer | % of punctuation marks in the tweet segment |
| # Special punctuation | Integer | % of ! and ? punctuation marks, i.e. !!!!!??? |
| Positive Sentiment | Integer | Positive sentiment score of the ngrams |
| Negative Sentiment | Integer | Negative sentiment score of the ngrams |
| Category of Previous Segment | 1 Boolean/category | The category of the previous segment |
| Category of Previous Tweet/Same Author | 1 Boolean/category | The category of the last segment of the previous tweet of the same author |
| Category of Previous Tweet/Same Author | 1 Boolean/category | The category of the last segment of the previous tweet of the other author |

For example, the feature extracting module 206 may associate or extract the at least one feature from the one or more sentences by removing stop words, masking @usernames, masking uniform resource locators (URLs), masking emails, masking numbers, masking emoticons as positive, neutral, or negative. The feature extracting module 206 may associate a vector of features to each of the one or more sentences in the conversation.

Further, the conversation analysis system 200A is configured to analyze the conversation for multiple tasks simultaneously. The tasks may include, but not limiting to, a task for determining a status of an issue identified in the conversation, and a task for determining nature of the conversation. Hereinafter, the task for determining the status of an issue may be referred as a status issue task or a Task 1 interchangeably. Further, herein, the task for determining the nature of the conversation may be referred a dialogue act or task 2. The parameter determining module 208 is configured to provide or define at least one equation for each of the tasks. The at least one equation is a mathematical function capable of calculating value of at least one parameter for each of the tasks based on the extracted or associated features for the tasks.

For description purpose, two tasks are described here but the model or equations may be extended for any number of tasks. Let $x=(x_1, x_2, \ldots x_T)$ be the sequence of entities (e.g., words in a sentence) that need to be labeled. Let $y=(y_1, y_2, \ldots y_T)$ and $z=(z_1, z_2, \ldots z_T)$ be two sets of labels, i.e., first label and second label, for task x. The two set of labels when combined with x represent two tasks. The y is the label sequence of first task (or task 1) while z is the label sequence for the second task (or task 2). Therefore, the training dataset is a triplet of (x, y, z).

An equation 1 is defined for the task 1, and an equation 2 is defined for the task 2. Exemplary equations for the two tasks are shown below as the equation 1 and equation 2, respectively. Hereinafter, equation may be referred as model.

$$p_1(y, z|x, \theta^y, \psi) == \frac{1}{U^y(x)} \prod_{t=1}^{T} \exp\left( \sum_k \left( \underbrace{\theta_k^y f_k(x_t, y_{t-1}, y_t)}_{\text{task } y \text{ factor}} + \underbrace{\psi_k f_k(x_t, y_t, z_t)}_{\text{label dependency factor}} \right) \right)$$

Equation 1

$$p_2(y, z|x, \theta^z, \psi) == \frac{1}{U^z(x)} \prod_{t=1}^{T} \exp\left( \sum_k \left( \underbrace{\theta_k^z f_k(x_t, y_{t-1}, y_t)}_{\text{task } z \text{ factor}} + \underbrace{\psi_k f_k(x_t, y_t, z_t)}_{\text{label dependency factor}} \right) \right)$$

Equation 2

Here $\theta_k^y, \theta_k^z$, and $\psi$ are parameter vectors and $f_k$, is a feature function/vector. It is important to note that the parameters $\theta_k^y$, and $\theta_k^z$ are task specific while parameter $\psi$ is common to both tasks 1, and 2 in shared version. As shown, the $\psi$ parameters of the equations 1, 2 share the information among different tasks. A pictorial representation 214 of these two models or equations 1, 2 is shown in FIG. 2C.

The parameter determining module 208 is further configured to determine value of the each of the one or more parameter vectors (or parameters) for each of the tasks. The parameters may be a property specific to a feature of the tasks. The parameter determining module 208 may determine the values of the at least one parameter by processing the multiple equations such as the, equation 1 and equation 2, simultaneously. In an embodiment, the equation 1 and equation 2 are processed for a pre-defined number of iterations. The parameter determining module 208 may be configured to optimize the values of the at least one parameter by performing alternate optimization. In alternate optimization, one-step to optimize the parameters of the equation 1 and then take one-step to optimize parameters of the equation 2. The whole process of the alternate optimization may be repeated for a fixed number of iteration. Further, during the optimization step, the parameters are optimized to maximize the log likelihood '$l_1$' and '$l_2$' of the equation 1, and equation 2 (or models 1, 2), respectively, on the training dataset.

$$\ell_1 = \sum_{i=1}^{n} \log p_1(y_i, z_i | x_i, \theta^y, \psi) - \eta^y \|\theta^y\|^2 + \lambda \|\psi\|^2$$

-continued $$\ell_2 = \sum_{i=1}^{n} \log p_2(y_i, z_i \mid x_i, \theta^z, \psi) - \eta^z \|\theta^z\|^2 + \lambda \|\psi\|^2$$

In some embodiments, the standard optimization method such as gradient descent method is used. Further, since both the equations 1 and 2 (models 1, 2), share some parameter, i.e., label dependency factor, hence alternate optimization is done. However, both the likelihood functions '$l_1$' and '$l_2$' are convex in themselves but alternate optimization technique is not guaranteed to converge.

In an embodiment, an unshared version is guaranteed to converge since there is no parameter sharing. In the equations of the unshared version there may not be any common parameter, i.e., '$\psi$' is different for different tasks.

The labeling module 210 is configured to assign one or more labels to each of the one or more sentences (being analyzed) based on the determined value of the at least one parameter. The one or more labels may include a first label and a second label. The first label is selected from a number of first labels) and the second label is selected from the second labels. The first labels may be used to label the parameters of the status issue task (or task 1). The second labels may be used to label the parameters of the dialogue act task (or task 2). The first labels and the second labels are defined in Table 2 and Table 3, respectively. The Table 2 includes the first labels and reflects the status of conversation (or one or more sentences) exchanged between the customer care agent 110 and the customers 112A-112N. The categories mentioned in the Table 2 gives information about how the problem is open by the customer goes at the time of the conversation. Since the status of the conversation can be updated after receiving each conversation (one or more sentences), the labeling module 210 may label each statement that is part of the conversation.

TABLE 2

| First label Category | Description | Example |
| --- | --- | --- |
| Open | When a conversation is ongoing and a further message is expected to follow | @Daleglass07 Hi, that's not good. |
| Solved | When the current message solves the problem mentioned in the current conversation, without requiring any further message | No, your payment would just increase by $5 a month and you will keep your Shrinkage milestone. |
| Closed | When the current message closes the conversation, even if the problem is not solved | @UNCRWNDKINGS We would rally hate to see you go. |
| Change Channel | When the CRM agent asks the customer to change channel by sending an email or a direct message. In this case, the conversation halts since further exchanges are on other private channels. | Can you please email me directly at bstsocialcare@sprint.com and I will gladly look into this. |

As shown below, the Table 3 includes the second labels or categories (also referred as Dialogue act labels) for labeling the one or more sentences based on the nature of the conversation. A person ordinarily skilled in the art will appreciate that the label categories in the Table 2 and Table 3 are not the exhaustive categories for first labels and second labels, respectively, and may include more or less categories.

TABLE 3

| Second label Category | Description | Example |
| --- | --- | --- |
| Complaint | When a customer complains | @vmucare I've sent an email, but I am absolutely disgusted with the customer care I am receiving |
| Apology | When an agent apologies | @kristenmchugh22 I do apologize for the inconvenience. |
| Answer | When someone answers a request | @BoostCare yea, allow my texts and calls to go out |
| Receipt | When someone acknowledges receipt | @VMUcare ok |
| Compliment | When someone sends a compliment | I still love VM and my intercept |
| Response to positivity | When someone acknowledges a previous positive message | @harryruiz No problem! |
| Request | When someone requests information | Please help me out. |
| Greeting | Greetings | @LucusHughes13 Hi there! |
| Thank | When someone expresses thanks | Thank you for being so patient. |
| Announcement | When a customer announces an information | @VMUcare phone stolen last night |
| Solved | When a message clearly states that a problem is solved | Close one! |
| Other | Any other message | Wow! |

The labeling module 210 may assign the second label by selecting one of the second labels from the Table 3 based on a linguistic theory of the conversation analysis. The second label(s) indicate the nature of each of the one or more sentences of the conversation. Further, the one or more sentences in the conversation may convey several information that cover several second categories (or labels) as defined in Table 3. For example, in a conversation (or one or more sentences) a customer care agent 110 can respond to a complaint by: i) greeting the customer, ii) then apologizing for the problem, and iii) requesting more detailed information concerning the problem. Accordingly, the labeling module 210 will analyze the one or more sentences (e.g., tweet segment in a conversation that happens over Twitter social networking website) and may assign three labels, i.e., 'Greeting', 'Apology', and 'Request', respectively.

Figure 2B:
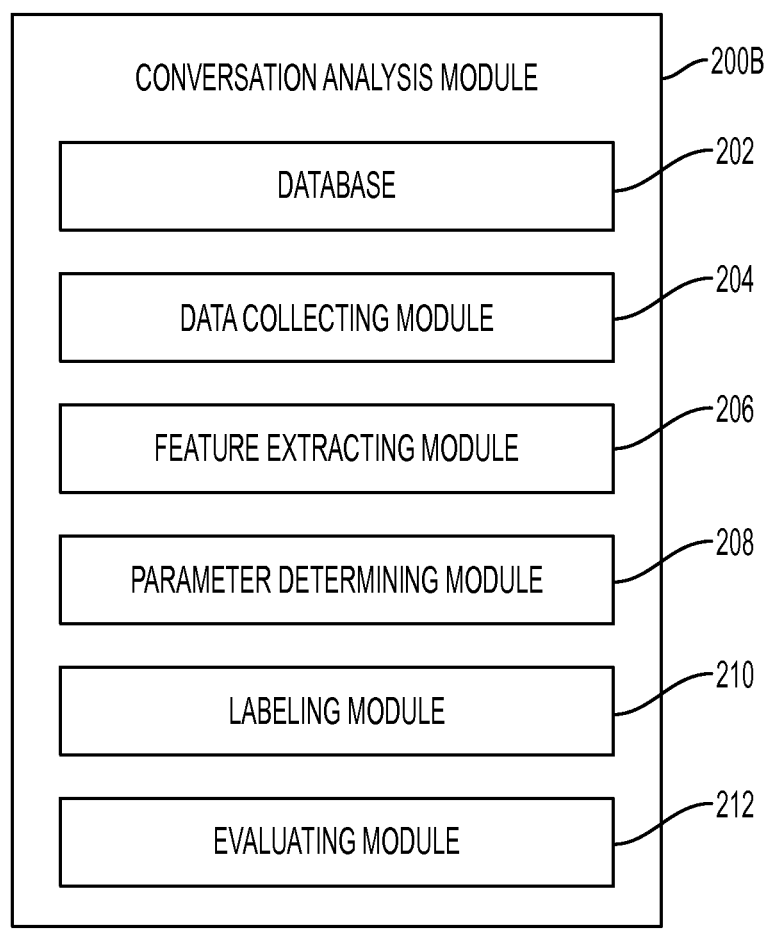
FIG. 2B is a schematic illustrating structural components of a conversation analysis system, in accordance with another embodiment of the present disclosure.
Figure 2C:
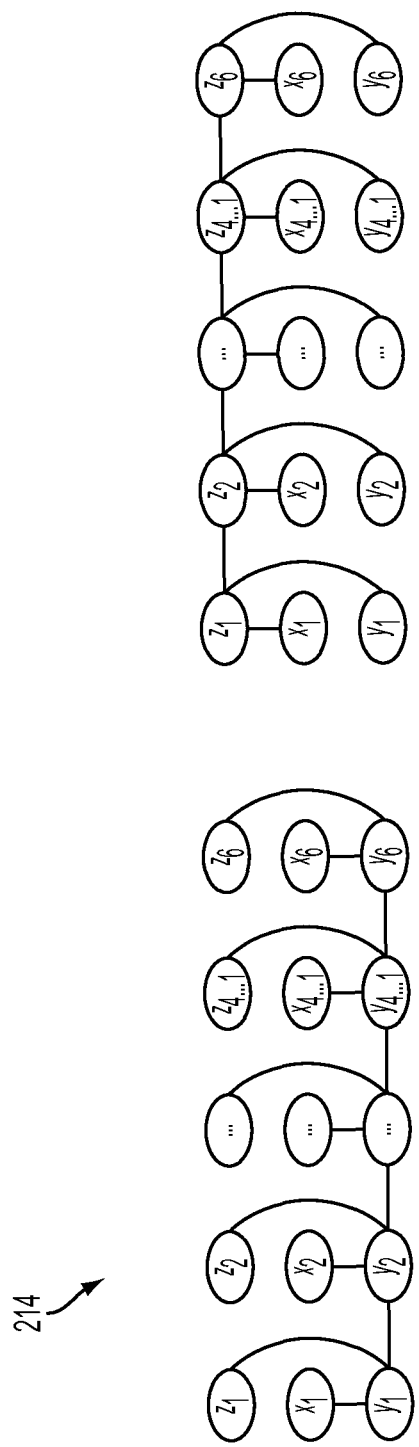
FIG. 2C is an exemplary pictorial representation in of disclosed models or equations, in accordance with an embodiment of the present disclosure.

Turning now to FIG. 2B, the evaluating module 212 is configured to evaluate the determined value of the at least one parameter of the task 1 and task 2 by comparing the determined value of the at least one parameter with the pre-defined value of the at least one parameter store in the database 202. The pre-defined value of the at least one parameter may be obtained based on the test dataset. In an embodiment, the test dataset includes a set of sentences that are analyzed using conventional models for conversation analysis.

Further, the conversation analysis system 200A or 200B may include software, hardware, firmware and combination of these. Further, the conversation analysis system 200A-200B can be unitary system or may be distributed over various devices such as, but not limiting to, servers in the network 104.

Figure 3:
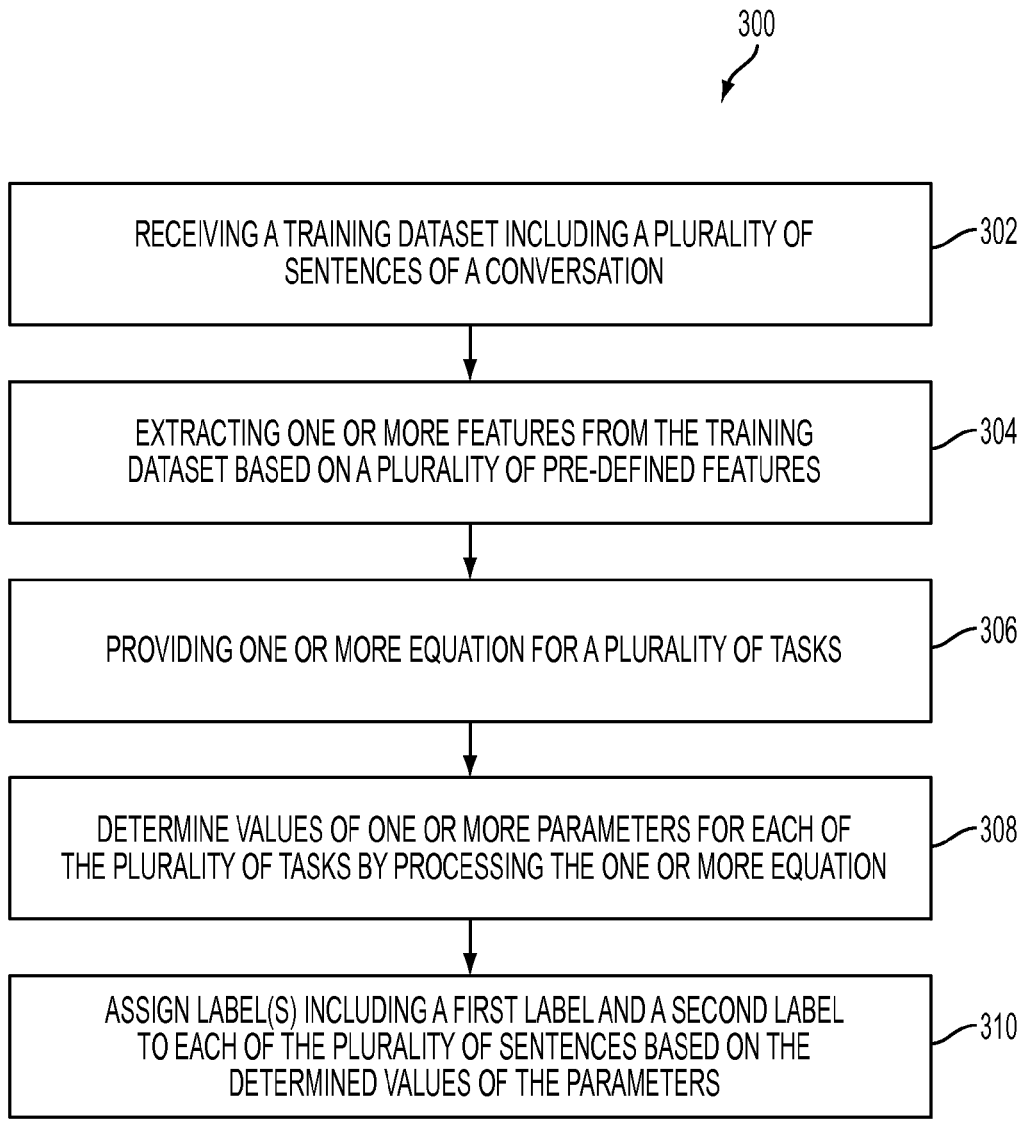
FIG. 3 is a flowchart illustrating a method for analyzing a plurality of sentences of a conversation, in accordance with an embodiment of the present disclosure.

FIG. 3 is a flowchart illustrating a method 300 for analyzing a number of sentences of a conversation, in accordance with an embodiment of the present disclosure. As discussed with reference to FIGS. 1A, 1B, 2A and 2B, various users 102A-102N or the customer agent 110 and the customers 112A-112N may communicate with each other via the social media 106 such as the Twitter. The conversations may get stored and then may be available for analysis. The conversation analysis system 108 (or 202A, 202B) is configured to analyze the conversations of the customer care agent 110 and the customers 112A-112N (or the users 102A-102N). Further, the conversation analysis system includes multiple modules 202-212 as described in FIGS. 2A-2B.

At step 302, a training dataset is received by the data collecting module 204 of the conversation analysis system 108. The training data set may include a natural language text sequence including one or more sentences of a conversation that happen between the customer care agent 110 and the customers 110A-110N. Each of the plurality of sentences include a number of words. For the sake of description only, analysis of the conversation between the customer care agent 110 and the customers 112A-112N are described, but the disclosed methods and systems may be used for analysis of any type of conversation that may happen between one or more users.

At step 304, the feature extracting module 206 may extract or assign at least one feature from/to the one or more sentences of the training dataset. Further, the feature extracting module 206 may extract the features based on the pre-defined features as mentioned in the Table 1 above.

Further, at step 306, at least one equations for each of the tasks, i.e., task 1 and task 2, are provided by the parameter determining module 208. Exemplary equations 1 and 2 are described above. Further, equation 1 and 2 include various parameter vectors and feature functions. At step 308, the parameter determining module 208 may determine value of the at least one parameter based on the extracted features. Further, the values of the parameters are determined by processing the equation 1 and equation 2. In an embodiment, the processing of the equations 1, 2 may take in multiple steps performed for a fixed number of iterations.

Then at step 310, the labeling module 210 may assign one or more label(s) to each of the sentences of the conversation, which is being analyzed, based on the determined value of the parameters as determined in the step 308. In some embodiments, the one or more labels include a first label and a second label. Further, the first label may be assigned from the first labels shown in Table 2 and the second label may be assigned from the second labels shown in the Table 3.

Figure 4:
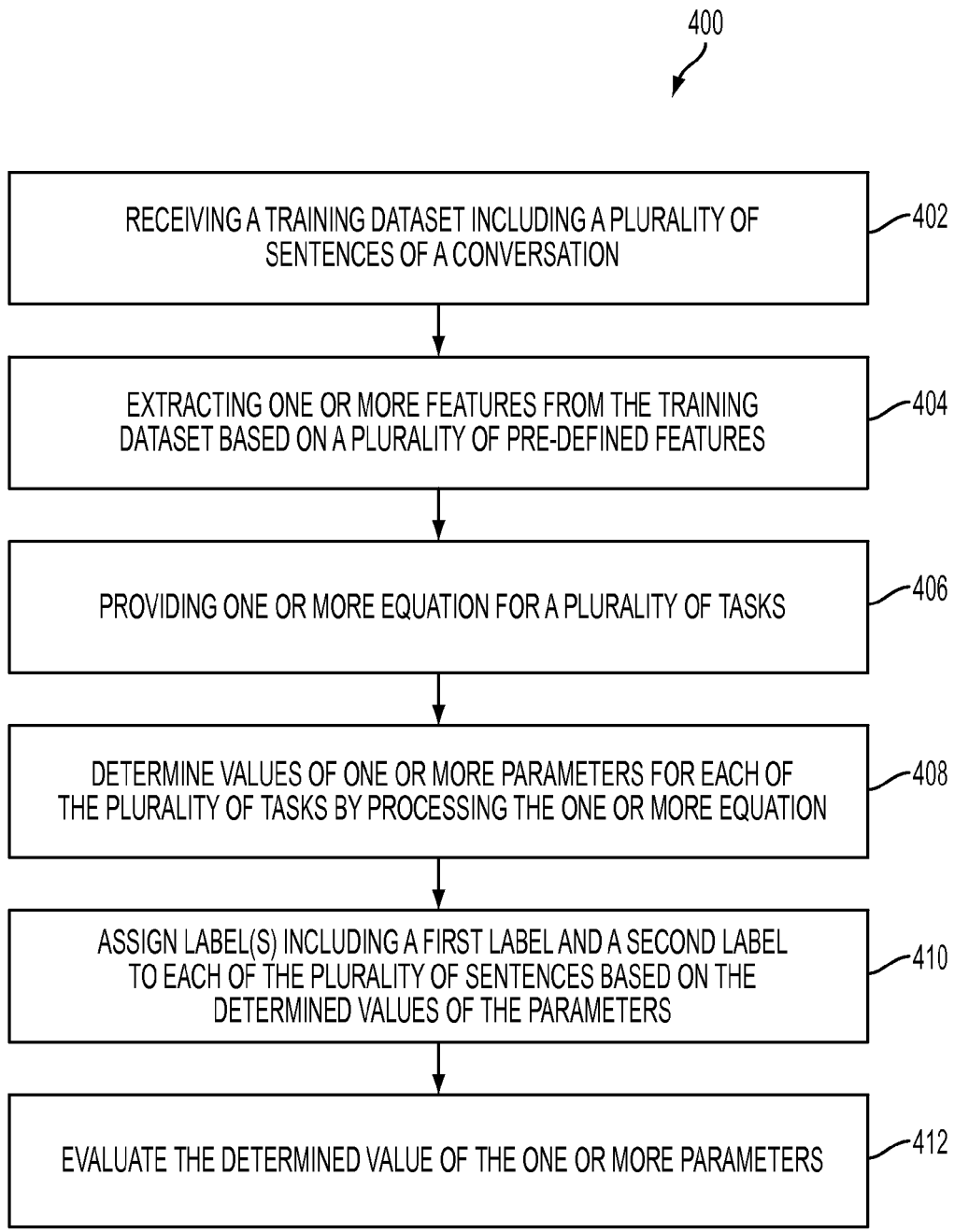
FIG. 4 is a flowchart illustrating a method for analyzing a plurality of sentences of a conversation, in accordance with another embodiment of the present disclosure.

FIG. 4 is a flowchart illustrating a method 400 for analyzing one or more sentences of a conversation, in accordance with an embodiment of the present disclosure. The steps 402, 404, 406, and 408 of the method 400 are similar to the steps 302-308 of the method 300 and are described in detail in FIG. 3.

At step 410, the evaluating module 212 may evaluate the determined value of the at least one parameter by comparing the determined value of the at least one parameter with the pre-defined value of the at least one parameter stored in the database. The pre-defined value of the at least one parameter are obtained based on the test dataset. In an embodiment, the test dataset includes a set of sentences that are analyzed using conventional models for conversation analysis.

In an embodiment, the parameter determining module 208 may be configured to optimize the determined value of the at least one parameter by performing alternate optimization. In alternate optimization, one-step to optimize the parameters of the equation 1 and then take one-step to optimize parameters of the equation 2. The whole process of the alternate optimization may be repeated for a fixed number of iteration. Further, during the optimization step, the parameters are optimized to maximize the log likelihood '$l_1$' and '$l_2$' of the equations 1, 2 (or models 1, 2), respectively, on the training dataset.

$$\ell_1 = \sum_{i=1}^n \log p_1(y_i, z_i \mid x_i, \theta^y, \psi) - \eta^y \|\theta^y\|^2 + \lambda \|\psi\|^2$$

$$\ell_2 = \sum_{i=1}^n \log p_2(y_i, z_i \mid x_i, \theta^z, \psi) - \eta^z \|\theta^z\|^2 + \lambda \|\psi\|^2$$

In some embodiments, the standard optimization method such as gradient descent method is used. Further, since both the equations 1, 2 (or models 1, 2), share some parameter, i.e., label dependency factor, hence alternate optimization is done. However, both the likelihood functions '$l_1$' and '$l_2$' are convex in themselves but alternate optimization technique is not guaranteed to converge.

In an exemplary scenario, the data collecting module 204 may collect the conversation data, which is exchanged between various users such as the customer care agent 110 and the customers 112A-112N over the social media 106 such as the Twitter social networking website (herein after Twitter). The conversations are then may be stored at the database 202 by the data collecting module 204 for further processing. For example, a training dataset may include 2780 statements (or tweet segments) of the conversation on the Twitter for processing. The training dataset is then analyzed for feature extraction by the feature extracting module 206. The feature extracting module 206 analyses the 2780 statements sentence by sentence (or at twitter segment level). The features are extracted or assigned based on the features stored in the database 202. The exemplary features are mentioned above in Table 1. In an exemplary scenario, the sentences are processes by lowering the case of all the words in the conversation, by removing stop words, by masking @username, passwords, URLs, emails, numbers, emoticons, etc. The emoticons may be masked as positive, neutral, or negative.

The equations 1 and 2 are defined for the task 1 and task 2 and are then processed using the extracted features. Further, the multiple tasks, i.e., task 1 and task 2 have same feature vectors and they only differ in labels. The values of the parameters is determined by processing the equation 1 and equation 2. Then, the values of the parameters may be optimized by alternate optimization.

Figure 5:
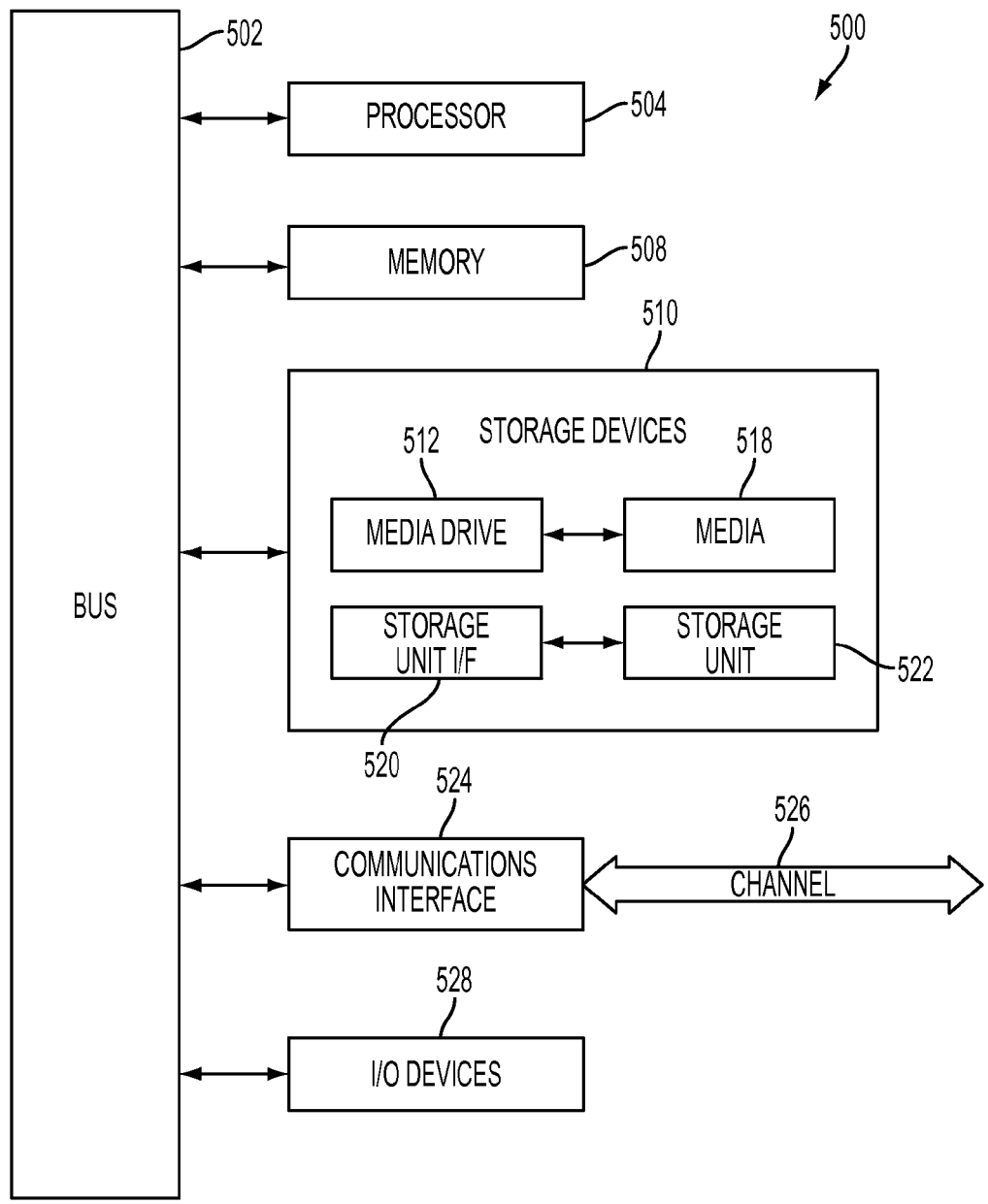
FIG. 5 illustrates a functional block diagram of a device and system on a network in which the present disclosure can find application.

FIG. 5 illustrates a functional block diagram of a device and system on a network in which the present disclosure can find application. FIG. 5 further illustrates an exemplary computing system or a networked conversation analysis system 500 such as those described in FIGS. 1A, 1B, 2A, and 2B that may be employed to implement processing functionality for various embodiments of the disclosed subject matter. For example, the computing system 500 is configured to analyze conversations between a number of users. The computing system 500 may represent, for example, a user device such as a personal computer, a smart phone, a laptop computer, a tablet computer, a server device, a server, shared memories, multi-function device, controllers for such devices or any other type of special or general purpose computing device as may be desirable or appropriate for a given application or environment.

The computing system 500 can include one or more processors, such as a processor 504. The processor 504 can be implemented using a general or special purpose processing engine such as, for example, a microprocessor, microcontroller or other control logic. In this example, the processor 504 is connected to a data pathway (e.g., buses, Ethernet) 502 or other communication medium. Although only one processor 504 is shown, in certain embodiments, the computing system may include more processors in an expanded or distributed design.

The computing system 500 can also include a main memory 506, preferably random access memory (RAM) or other dynamic memory, for storing information and instructions to be executed by the processor 504. The processor 504 accepts instructions and data from the memory 506 and performs various data processing functions of the system. These data processing functions may include, but are not limited to, providing graphical format objects via a graphical user interface, creating a graphical representation for a plurality of attributes, defining values of attributes based on selection of the graphical representation, executing operation on the computing system based on graphical representation and values of attributes, and so forth. The processor 504 includes an arithmetic logic unit (ALU) that performs arithmetic and logical operations, and a control unit that extracts instructions from the memory 506 and decodes and executes them, calling on the ALU when necessary. The main memory 506 also may be used for storing temporary variables or other intermediate information during execution of instructions to be executed by the processor 504. The memory 506 stores a variety of data received by the computing system 500 and computed by the various data processing functions of the computing system 500. The data may include, for example, values of attributes, graphical format objects, graphical representations, and so forth.

The computing system 500 may likewise include a read only memory ("ROM") or other static storage device coupled to the data pathway 502 for storing static information and instructions for processor 504. Also, the memory 506 preferably contains an operating system, which executes on the processor 504. The operating system performs basic tasks that include recognizing input, sending output to output devices, keeping track of files and directories and controlling various peripheral devices.

The computing system 500 may also include information storage mechanism 510, which may include, for example, a media drive 512 and a removable storage interface 520. The media drive 512 may include a drive or other mechanism to support fixed or removable storage media, such as a hard disk drive, a floppy disk drive, a magnetic tape drive, an optical disk drive, a CD or DVD drive (R or RW), or other removable or fixed media drive. A storage media 516 may include, for example, a hard disk, floppy disk, magnetic tape, optical disk, CD or DVD, or other fixed or removable medium that is read by and written to by media drive 512. As these examples illustrate, storage media 516 may include a computer-readable storage medium having stored there in particular computer software or data.

In alternative embodiments, information storage mechanism 510 may include other similar instrumentalities for allowing computer programs or other instructions or data to be loaded into the computing system 500. Such instrumentalities may include, for example, a removable storage unit 522 and an interface 520, such as a program cartridge and cartridge interface, a removable memory (for example, a flash memory or other removable memory module) and memory slot, and other removable storage units 522 and the interfaces 520 that allow software and data to be transferred from removable the storage unit 522 to the computing system 500.

The computing system 500 can also include a communications interface 524 that enables the computing system 500 to access other computers and resources on a communication network. The communications interface 524 can be used to allow software and data to be transferred between computing system 500 and external devices. Examples of the communications interface 524 can include a modem, a network interface (such as an Ethernet or other NIC card), a communications port (such as, e.g., a USB port), a PCMCIA slot and card, etc. Software and data transferred via communications interface 524 are in the form of signals which can be electronic, electromagnetic, optical, or other signals capable of being received by communications interface 524. These signals are provided to communications interface 524 via a channel 526. This channel 526 may carry signals and may be implemented using a wireless medium, wire or cable, fiber optics, or other communications medium. Some examples of a channel include a phone line, a cellular phone link, an RF link, a network interface, a local or wide area network, and other communications channels. What is important is that the various computers and peripherals can interact to perform various document services.

The computing system 500 further includes input/output devices 528 such as a keyboard and a mouse that enables a user to enter data and instructions into the computing system 500, a display device that enables the user to view the available information, and a printer that enables the user to print any data for his reference. Alternatively, input/output devices 528 may include a touch sensitive display that enables a user to enter data and instructions into the computing system 500 as well as to view the available information.

In this document, the terms "computer program product" and "computer-readable medium" may be used generally to refer to media such as, for example, the memory 506, the storage device 516, the storage unit 522, or signal(s) on the channel 526. These and other forms of computer-readable media may be involved in providing one or more sequences of one or more instructions to the processor 504 for execution. Such instructions, generally referred to as "computer program code" (which may be grouped in the form of computer programs or other groupings), when executed, enable computing system 500 to perform features or functions of embodiments of the disclosed subject matter.

In an embodiment where the elements are implemented using software, the software may be stored in a computer-readable medium and loaded into the computing system 500 using, for example, removable storage drive 514, the drive 512 or the communications interface 524. The control logic (in this example, software instructions or computer program code), when executed by processor 504, causes processor 504 to perform the functions of the disclosed subject matter as described herein.

An aspect of the present disclosure allows real-time computation of content based metrics for the conversation that happen between the customer care agent(s) and the customer(s) (or users).

Another aspect of the present disclosure, not only exploits the label dependency factor but also learns the multiple tasks simultaneously by explicitly sharing the parameters corresponding to the label dependency factor. In the proposed methods, one model is learnt for each task. Each model may include a set of factors for its own task with one additional factor for the label dependency part. The parameters corresponding to the label dependency factor is common among all tasks.

A yet another aspect of the present disclosure provides an unshared version model where there is no parameter sharing but only label dependency is there.

A further aspect of the present disclosure provides a method for learning from shared tasks for sequence labeling tasks.

In an embodiment, the determined value of the parameters is evaluated. The values may be evaluated by comparing the results of the disclosed systems (or models) with state of the art baselines and report results. Accuracy may be used as a metric for evaluation. Further, a test dataset may be used for evaluating the accuracy of the values of the parameters or labeling. Accuracy may be defined as fraction of correctly labeled tokens/sentences in sequence present in bigrams present in the test set.

It will be understood that the modules and the databases referred to in the previous sections are not necessarily utilized together in a single conversation analysis system. Rather, these modules are merely exemplary of the various modules that may be implemented within a conversation analysis system. Further, it will be understood that the conversation analysis module may include more modules than the ones described in this disclosure without departing from the scope of the present disclosure.

It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art, which are also intended to be encompassed by the following claims.

What is claimed is:

1. A method for analyzing a natural language text sequence of a conversation exchanged between multiple users of a platform, the method comprising:
   extracting, by one or more processors, at least one feature from a training dataset that includes a natural language text sequence of a conversation exchanged between multiple users of a platform based on a pre-defined features stored at a database, wherein the natural language text sequence comprises a plurality of sentences, each of the plurality of sentences including a number of words;
   defining, by the one or more processors, at least one equation for two or more tasks to be completed;
   calculating, by the one or more processors, a parameter value for each of the two or more tasks using the equation, the parameter value being based on the at least one feature extracted from the training dataset;
   selecting, by the one or more processors, one or more first labels from a plurality of first labels and one or more second labels from a plurality of second labels based on the calculated parameter value and applying the selected one or more first and second labels to each of the plurality of sentences of the natural language sequence of the training dataset; and
   based on the selected one or more first and second labels, indicating to the multiple users of the platform, by the one or more processors, that the two or more tasks are complete.

2. The method of claim 1, wherein the at least one feature is extracted based on the plurality of pre-defined features, the plurality of pre-defined features including at least one of a 'Word 1-grams and 2-grams', 'Segment position in thread', 'Segment position in tweet', 'Sender', 'Contains email', '#Upper case', '#Punctuation', '#Special punctuation', 'Positive Sentiment', 'Negative Sentiment', 'Category of previous segment', 'Category of previous tweet/author', and 'Category of previous tweet'.

3. The method of claim 2, wherein the two or more tasks include at least one of a task to determine a status of an issue in the conversation exchanged between multiple users of the platform, and a task to determine a nature of the conversation exchanged between multiple users of the platform.

4. The method of claim 3, wherein calculating the parameter value includes processing, by the one or more processors, the at least one equation for the two or more tasks for a pre-defined number of iterations.

5. The method of claim 4, wherein the plurality of first labels comprises at least one of 'Open', 'Solved', 'Closed', and 'Changed channel'.

6. The method of claim 5, wherein the plurality of first labels are associated with the at least one task of determining determine a status of an issue.

7. The method of claim 6, wherein the plurality of second labels comprises at least one of a 'Complaint', 'Apology', 'Answer', 'Receipt', 'Compliment', 'Response to positivity', 'Request', 'Greeting', 'Thank', 'Announcement', 'Solved', and 'Other'.

8. The method of claim 7, wherein the plurality of second labels are associated with the at least one task of determining the nature of the conversation.

9. The method of claim 8, wherein the at least one equation includes a common parameter for each of the two or more tasks to be completed.

10. The method of claim further comprising:
    comparing, by one or more processors, the calculated parameter value for each of the two or more tasks to a pre-defined parameter value stored at the database, the pre-defined parameter value being calculated based on an evaluation of a test dataset, wherein the test dataset includes a pre-defined set of sentences that each include at least one word.

11. The method of claim 10, wherein the natural language text sequence of the training dataset includes a natural language text sequence of a conversation exchanged between a customer care agent and multiple customers of a platform, wherein the natural language text sequence of the conversation exchanged between the customer care agent and multiple customers of a platform comprises a plurality of sentences exchanged between the customer care agent and multiple customers using a social media platform.

12. A system for automated analysis of a natural language text sequence of a conversation exchanged between multiple users of a platform, the system comprising:
    one or more processors configured to:
       store a plurality of pre-defined features, two or more tasks to be completed, a plurality of first labels, and a plurality of second labels;
       extract at least one feature from a training dataset based on the plurality of pre-defined features stored at the database, wherein the training dataset includes a natural language text sequence of a conversation exchanged between multiple users of a platform, the natural language text sequence including a plurality of sentences;
       define at least one equation for the two or more tasks to be completed;
       calculate a parameter value for each of the two or more tasks using the equation, the parameter value being calculated based on the at least one extracted feature and stored at the database;

select one or more first labels from the plurality of stored first labels and one or more second labels from the plurality of stored second labels based on the calculated parameter value;

apply the selected one or more first and second labels to each of the plurality of sentences of the natural language text sequence of the training dataset; and indicate to the multiple users of the platform when the two or more tasks are complete, the indication being based on the applied first and second labels.

13. The system of claim 12, wherein the at least one feature is extracted based on the plurality of pre-defined features, the plurality of pre-defined features including at least one of a 'Word 1-grams and 2-grams', 'Segment position in thread', 'Segment position in tweet', 'Sender', 'Contains email', '#Upper case', '#Punctuation', '#Special punctuation', 'Positive Sentiment', 'Negative Sentiment', 'Category of previous segment', 'Category of previous tweet/author', and 'Category of previous tweet'.

14. The system of claim 13, wherein the two or more tasks include at least one of a task to determine a status of an issue in the conversation exchanged between multiple users of the platform, and a task to determine a nature of the conversation exchanged between multiple users of the platform.

15. The system of claim 14, wherein calculating the parameter value further includes:
processing, by the one or more processors, the at least one equation for the two or more tasks for a pre-defined number of iterations.

16. The system of claim 15, wherein the plurality of first labels comprises at least one of 'Open', 'Solved', and 'Changed channel'.

17. The of claim 16, wherein the plurality of first labels are associated with the at least one task of determining a status of an issue.

18. The system of claim 17, wherein the plurality of second labels comprises at least one of a 'Complaint', 'Apology', 'Answer', 'Receipt', 'Compliment', 'Response to positivity', 'Request', 'Greeting', 'Thank', 'Announcement', 'Solved', and 'Other'.

19. The system of claim 18, wherein the plurality of second labels are associated with the at least one task of determining the nature of the conversation.

20. The system of claim 19, wherein the at least one equation includes a common parameter for each of the two or more tasks to be completed.

21. The system of claim 20, wherein the one or more processors are further configured to:
compare the calculated parameter value for each of the two or more tasks to a pre-defined parameter value stored at the database, the pre-defined parameter value being calculated based on an evaluation of a test dataset, wherein the test dataset includes a pre-defined set of sentences stored at the database that each include at least one word.

22. The system of claim 21, wherein the conversation exchanged between multiple users of a platform occurs between a customer care agent and one or more a plurality of customers of a platform, wherein the conversation includes a plurality of sentences exchanged between the customer care agent and one or more customers using a social media platform.

23. A method for automated analysis of one or more conversations exchanged between a customer care agent and multiple customers of a social media platform, the method comprising:

collecting, by one or more processors, a first training dataset having a natural language text sequence of a conversation exchanged between the customer care agent and at least one of the multiple customers of the social media platform;

extracting, by the one or more processors, one or more pre-defined features stored at a database from the first text sequence;

defining, by the one or more processors, at least one equation that includes a common parameter for each of two or more tasks to be resolved by the customer care agent;

based on the extracted features, calculating, by the one or more processors, a first parameter value for a first task of the two or more tasks and a second parameter value for a second task of the two or more tasks using the equations defined for the two or more tasks;

assigning, by the one or more processors, one or more labels to the first text sequence based on the calculated first parameter value and the calculated second parameter value, a first label of the one or more labels being an issue status label and a second label of the one or more labels being a nature of a conversation status label;

sending, by the one or more processors, a status update to the customer care agent indicating a resolved status based on the one or more labels assigned to the first text sequence and the extracted features.

24. The method of claim 23, wherein the first text sequence of the conversation includes one or more sentences that form a training dataset, wherein the training dataset is received by the one or more processors in real time.

25. A system for automated analysis of one or more conversations exchanged between a customer care agent and multiple customers of a social media platform, comprising:
one or more processors configured to:
store a plurality pre-defined features, two or more tasks to be resolved, and one or more labels at a database;
collect a first text sequence of a conversation exchanged between the customer care agent and at least one of the multiple customers of the social media platform;
extract one or more pre-defined features from the plurality of pre-defined features stored at the database from the first text sequence;
define at least one equation that includes a common parameter for each of two or more tasks to be resolved by the customer care agent;
based on the extracted features, calculate a first parameter value for a first task of the two or more tasks and a second parameter value for a second task of the two or more tasks using the at least one equation defined for each of the two or more tasks;
assign one or more labels to the first text sequence based on the calculated first and second parameter values, a first label of the one or more labels being an issue status label and a second label of the one or more labels being a nature of the conversation status label; and
send an update to the customer care agent that the two or more tasks are resolved based on the one or more labels assigned to the first text sequence of the conversation exchanged between the customer care agent and the at least one customer of the social media platform.

26. The system of claim 25, wherein the first text sequence of the conversation includes one or more sentences that form a training dataset, wherein the training dataset is received by the one or more processors in real time.

27. A computer configured to perform an automated analysis of one or more conversations exchanged between a customer care agent and a plurality of customers of a platform, the computer comprising:
- a computer readable medium; and
- computer program instructions, recorded on the computer readable medium, executable by a processor, the processor configured to:
  - receive a training dataset that includes a natural language text sequence of a conversation exchanged between the customer care agent and a plurality of customers of a platform, wherein the natural language text sequence comprises a plurality of sentences that each include a number of words;
  - extract at least one pre-defined feature stored on the computer readable medium from the training dataset;
  - define at least one equation for each of two or more tasks to be resolved by the customer care agent;
  - calculate one or more parameter values for the two or more tasks using the defined equations, wherein the calculated parameter values are based on the extracted feature;
  - assign one or more labels to each of the sentences of the natural language text sequence based on the calculated one or more parameter values, wherein a first label of the one or more labels is an issue status label and a second label of the one or more labels is a nature of the conversation status label; and
  - update a status associated with the conversation exchanged between the customer care agent and at least one of the plurality of customers of the platform to resolved based on the assigned one or more labels and the extracted feature.

* * * * *